(12) United States Patent
Wanunu et al.

(10) Patent No.: US 10,570,444 B2
(45) Date of Patent: Feb. 25, 2020

(54) PINHOLE ZERO-MODE WAVEGUIDES

(71) Applicant: Northeastern University, Boston, MA (US)

(72) Inventors: Meni Wanunu, Boston, MA (US); Joseph Larkin, Dorchester, MA (US); Robert Henley, Boston, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 15/572,296

(22) PCT Filed: May 11, 2016

(86) PCT No.: PCT/US2016/031824
§ 371 (c)(1),
(2) Date: Nov. 7, 2017

(87) PCT Pub. No.: WO2016/183180
PCT Pub. Date: Nov. 17, 2016

(65) Prior Publication Data
US 2018/0135118 A1 May 17, 2018

Related U.S. Application Data

(60) Provisional application No. 62/159,731, filed on May 11, 2015.

(51) Int. Cl.
*C12Q 1/6869* (2018.01)
*G02B 6/10* (2006.01)
*B82Y 20/00* (2011.01)

(52) U.S. Cl.
CPC ............ *C12Q 1/6869* (2013.01); *B82Y 20/00* (2013.01); *G02B 6/107* (2013.01)

(58) Field of Classification Search
CPC .............................. C12Q 1/6869; B82Y 20/00
See application file for complete search history.

(56) References Cited

U.S. PATENT DOCUMENTS

| | | |
|---|---|---|
| 2004/0011651 A1 | 1/2004 | Becker et al. |
| 2010/0065726 A1* | 3/2010 | Zhong .................. G01N 21/648 250/227.24 |
| 2010/0075827 A1 | 3/2010 | Pellin et al. |
| 2011/0053284 A1 | 3/2011 | Meller et al. |
| 2013/0240356 A1 | 9/2013 | Wanunu et al. |

OTHER PUBLICATIONS

D.A. Wheeler et al., "The complete genome of an individual by massively parallel DNA sequencing", Nature, (2008), vol. 452, pp. 872-876.
C. Meldrum et al., "Next-Generation Sequencing for Cancer Diagnostics: a Practical Perspective", The Clinical Biochemist Reviews, Nov. 2011, vol. 32, pp. 177-195.
I.C. Macaulay et al., "G&T-seq: parallel sequencing of single-cell genomes and transcriptomes", Nature Methods, Jun. 2015, vol. 12, No. 6, pp. 519-522.
M. Kellis et al., "Defining functional DNA elements in the human genome", Proceedings of the National Academy of Sciences, Apr. 29, 2014, vol. 111, No. 17, pp. 6131-6138.
V.G. Leblanc et al., "Next-Generation Sequencing Approaches in Cancer: Where Have They Brought Us and Where Will They Take Us?", Cancers (2015), vol. 7, pp. 1925-1968.
A.L. Norris et al., "Nanopore sequencing detects structural variants in cancer", Cancer Biology & Therapy, (2016), vol. 17, No. 3, pp. 246-253.
M.J.P. Chaisson et al., "Resolving the complexity of the human genome using single-molecule sequencing", Nature, Jan. 29, 2015, vol. 517, No. 7536, pp. 608-611.
M. Pendleton et al., "Assembly and diploid architecture of an individual human genome via single-molecule technologies", Nat. Methods, Aug. 2015, vol. 12, No. 8, pp. 780-786.
H. Kawaji et al, "Comparison of CAGE and RNA-seq transcriptome profiling using clonally amplified and single-molecule next-generation sequencing", Genome Research, (2014), vol. 24, No. 4, pp. 708-717.
B.A. Flusberg et al., "Direct detection of DNA methylation during single-molecule, real-time sequencing", Nat. Methods, Jun. 2010, vol. 7, No. 6, pp. 461-465.
J. Beaulaurier et al., "Single molecule-level detection and long read-based phasing of epigenetic variations in bacterial methylomes", Nature Communications, Jun. 15, 2015, vol. 6, 12 pgs.
E.E. Schadt et al., "Modeling kinetic rate variation in third generation DNA sequencing data to detect putative . modifications to DNA bases", Genome Research, (2013), vol. 23, No. 1, 14 pgs.
J. Schreiber et al, "Error rates for nanopore discrimination among cytosine, methylcytosine, and hydroxymethylcytosine along individual DNA strands", Proceedings of the National Academy of Sciences, Nov. 19, 2013, vol. 110, No. 47, pp. 18910-18915.
Pacific Biosciences Template Preparation and Sequencing Guide, Pacific Biosciences of California, Menlo Park, CA, (2014), 52 pgs.
A. Meller et al., "Single molecule measurements of DNA transport through a nanopore", Electrophoresis, (2002), vol. 23, pp. 2583-2591.
E. Karlsson et al., "Scaffolding of a bacterial genome using MinION nanopore sequencing", Scientific Reports, Jul. 1, 2015, vol. 5, 8 pgs.
C. Raley et al., "Preparation of next-generation DNA sequencing libraries from ultra-low amounts of input DNA: Application to single-molecule, real-time (SMRT) sequencing on the Pacific Biosciences RS II", bioRxiv, Mar. 25, 2014, retrieved online from: www.dx.doi.org/10.11011003566.

(Continued)

*Primary Examiner* — Narayan K Bhat
(74) *Attorney, Agent, or Firm* — Verrill Dana, LLP

(57) ABSTRACT

Devices and methods useful for sequencing and characterizing single nucleic acid molecules involve large arrays of nanopore zero-mode waveguides (NZMWs). The methods and devices are made possible by fabrication of nanoporous membranes of appropriate porosity for use in nucleotide sequencing. The fabrication methods eliminate the need for serial nanopore formation and make possible the mass production of highly efficient DNA and RNA single molecule sequencing devices.

11 Claims, 6 Drawing Sheets

Specification includes a Sequence Listing.

(56) References Cited

OTHER PUBLICATIONS

J. Larkin et al., "Reversible Positioning of Single Molecules inside Zero-Mode Waveguides", Nano Letters, (2014), vol. 14, pp. 6023-6029.

M. Wanunu et al., "Rapid electronic detection of probe specific microRNAs using thin nanopore sensors", Nature Nanotechnology, Oct. 24, 2010, vol. 5, pp. 807-814.

O.N. Assad et al., "Two Color DNA Barcode Detection in Photoluminescence Suppressed Silicon Nitride Nanopores", Nano Letters, (2015), vol. 15, pp. 745-752.

M. Wanunu, "Nanopores: A journey towards DNA sequencing", Physics of Life Reviews, Jun. 2012, vol. 9, No. 2, pp. 125-158.

X. Liang et al., "Ultrathin highly porous alumina films prepared by alucone ABC molecular layer deposition (MLD)", Microporous and Mesoporous Materials, (2013), vol. 168, pp. 178-182.

\* cited by examiner

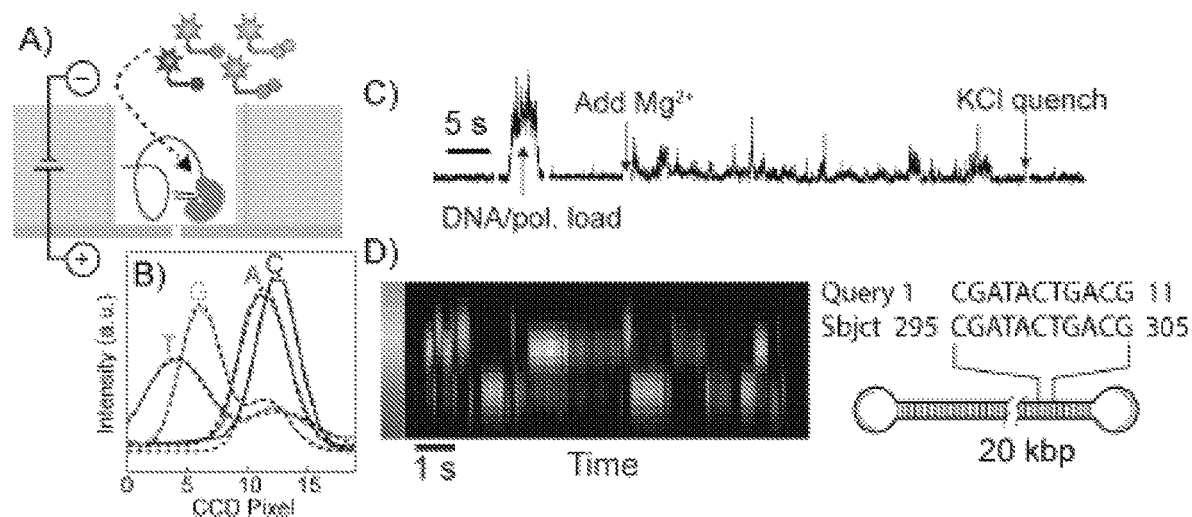
Figs. 5A – 5D
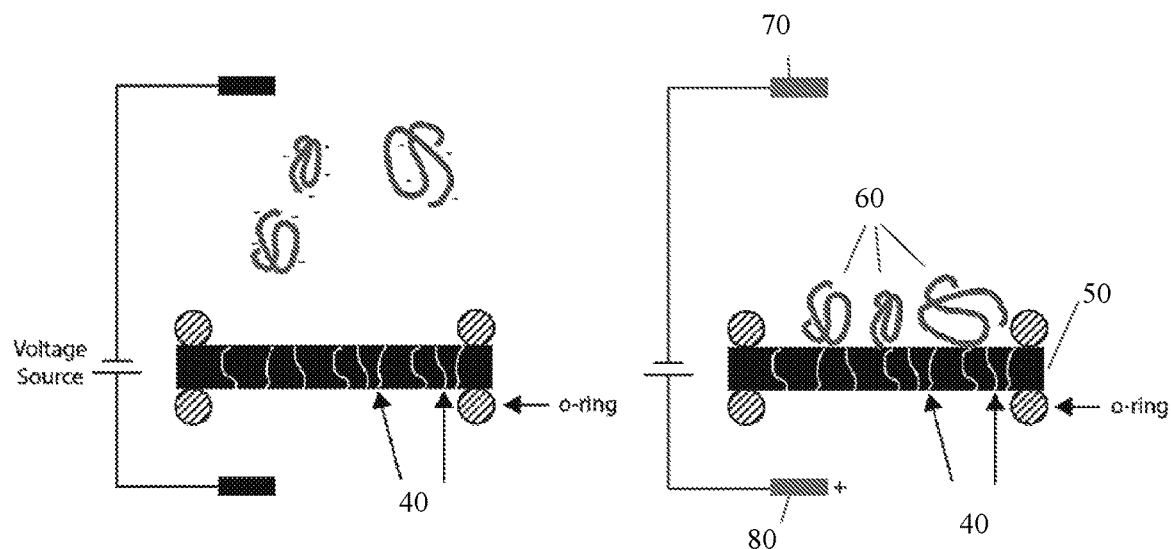
Fig. 6A
Fig. 6B

PINHOLE ZERO-MODE WAVEGUIDES

STATEMENT REGARDING FEDERALLY SPONSORED RESEARCH OR DEVELOPMENT

The invention was developed with financial support from Grant No. R21 HG006873 from the National Institutes of Health. The U.S. Government has certain rights in the invention.

BACKGROUND

Recent advances in genome technology have uncovered many variations among healthy and diseased cells, leading to breakthroughs in health care, such as new disease markers and drug targets, new tools for early diagnosis, and personalized therapeutics. Several studies using second-generation whole genome DNA sequencing and re-sequencing have compared DNA from healthy and cancerous cells, and the results have revealed tremendous structural variation, single-nucleotide polymorphisms, and multiple new mutations acquired by tumor cells, which distinguished healthy individuals from others (1-3). Information at the RNA level is also important for understanding mechanisms in the development of disease (4,5). For example, parallel DNA/transcriptome sequencing from a single cell has recently revealed links between gene variation and expression dynamics (6). A third layer of information lies within dynamic changes to the DNA and RNA bases during a cell's life; epigenetic modifications and DNA damage have impact on cell development, disease, and aging (7,8). These and other studies have played a major role in shaping our current vision of genomics, and have been enabled by major advances in high-throughput second-generation sequencing and concentrated efforts and consortia, such as through the ENCODE project) (9).

Third generation sequencing methods, by offering long read lengths and the ability to probe epigenetic states on single, native DNA molecules, have become indispensable tools in genomics (10,11). Probing individual molecules can enable future analysis of sequence and epigenetic information in DNA and RNA, ultimately from as little as a single living cell. However, several significant challenges remain.

Single molecule, real-time (SMRT) sequencing or nanopore-based DNA strand sequencing, by virtue of long read lengths, can resolve complex repeated elements and structural variants (12,13) that are difficult to assemble using second-generation sequencing tools. High sequence coverage and extended contig lengths facilitate gene discovery and whole genome assembly with unprecedented quality (14,15). Recently, Pacific Biosciences released a human genome assembly (60× coverage, read length N50 of 19 kb, and contig N50 of 26.9 Mb), which was critical for filling sequence gaps and uncovering human genome structural variation (14). These assays typically require making libraries from µg amounts of DNA samples. Similarly, targeted sequencing studies also typically require substantial amounts of DNA as starting material, and for cases where that cannot be accommodated, amplification is used to generate enough DNA for library preparation and sequencing.

Third-generation sequencing methods enable quantitative transcriptome analysis by sequencing cDNA libraries with longer reads than second-generation methods. While a recent comparison of second and third generation RNA sequencing methods found comparable performance in terms of bias in gene expression levels (16), long-read third-generation sequencing allows full-length transcripts to be decoded, facilitating assembly-free isoform reconstruction (17). Recently, direct SMRT sequencing of RNA was demonstrated using a reverse transcriptase (RT), showing RNA base modification detection; however, several significant limitations were noted in this feasibility study, including the slow speed, short read lengths, inability to discriminate base repeats, and insensitivity to RNA secondary structures (18).

SMRT sequencing has greatly impacted microbial epigenetics by allowing resolution of methylation patterns in adenines and cytosines, predominantly in prokaryotic DNA (19-21). Oxidative damage and other base lesions in mitochondrial DNA (mtDNA) have a profound impact on understanding disease and aging (22), and SMRT sequencing has been applied to detect mtDNA lesions in single DNA molecules (sequence variation, indels, and damaged bases) (23). Nanopores have also demonstrated methylation detection (24, 25), although the discrimination accuracy is sequence specific, and a general detection platform is not available to date. RNA epigenetic modifications are also common, and thought to play important roles (26), though less is known about these because RNA is typically converted to cDNA, in which modifications are lost. The impact of third generation sequencing applications on understanding the role of epigenetics in mammalian diseases is therefore significantly restricted by prohibitively high input sample requirements or chemical conversion requirements (e.g., amplification and bisulfite treatment) prior to sequencing.

A major challenge common to TGS methods is the inefficiency with which sub-ng input libraries are sequenced. Both SMRT sequencing and nanopore sequencing rely on capture of DNA/RNA into a nanoscale detector. For SMRT sequencing, DNA/polymerase complexes need to be chemically tethered at the bottom of 100 nm diameter nanowells called zero-mode waveguides (ZMWs). Due to geometric constraints, the efficiency of DNA diffusion and binding to the ZMW base sharply decreases for DNA fragments longer than 2 kb (27). Use of magnetic beads provides an approximately 10-fold increase in loading efficiency, although this still prohibits sub-ng level sequencing. Nanopore sequencing relies on threading a single-stranded tail into a 1.5 nm diameter pore, a process that is inherently improbable due to DNA entropy and the small nanopore constriction (28). The amounts of DNA required for current nanopore sequencing methods are orders of magnitude higher than amounts in a human cell (6 pg of DNA and comparable amounts of RNA (30)). Therefore, while library preparation from sub-ng DNA is available (31), sample loss in library preparation steps and DNA loading inefficiency have called for sample amplification in both nanopore-based (32) and SMRT sequencing (27) platforms for very low-input samples. Efficient loading and sequencing of native picogram-level DNA/RNA libraries would constitute a major milestone in genomics by providing a multidimensional palette of genomic, transcriptomic, and epigenomic data from small samples, including single cells.

SUMMARY OF THE INVENTION

The invention provides devices and methods useful for sequencing and characterizing single nucleic acid molecules. The methods of the invention enable highly efficient sequencing of single nucleic acid molecules, and are carried out using large arrays of nanopore zero-mode waveguides (NZMWs). The methods and devices are made possible by fabrication of nanoporous membranes of appropriate porosity for use in nucleotide sequencing, which eliminates the need for serial nanopore formation. The invention utilizes anisotropic etching techniques, such as reactive ion etching, or deposition of non-ideal thin films with controlled defects, giving rise to membranes with a plurality of nanometer scale or sub-nanometer scale pinholes or nanopores. NZMW chambers are then fabricated onto the membrane to create large NZMW arrays.

One aspect of the invention is a nanoporous membrane. The membrane contains a plurality of nanopores through the material of the membrane. The nanopores have a diameter in the range from about 0.3 nm to about 15 nm and provide substantially the only ion conductive pathways across the membrane. In preferred embodiments, the membrane is ultrathin and made of an inorganic material, such as oxide of aluminum, hafnium, or silicon. In preferred embodiments, the nanopores result from the fabrication of the membrane. In preferred embodiments, the nanopores are not made with the use of an electron beam, ion beam, or laser. In preferred embodiments, the nanopores are made with the use of a dry etch or wet etch method. In preferred embodiments, the membrane is fabricated using atomic layer deposition or molecular layer deposition.

Another aspect of the invention is a zero-mode waveguide device. The device includes first and second fluid chambers separated by the nanoporous membrane described above. The dimensions of the first chambers are consistent with their use as zero-mode waveguides to optically investigate biomolecules in a fluid of the first chambers.

Yet another aspect of the invention is a zero-mode waveguide device comprising a plurality of first fluid chambers disposed in a two-dimensional array on a single chip and a single common second fluid chamber, the first and second fluid chambers separated by the nanoporous membrane. In a preferred embodiment, the membrane is continuous across the chip. In embodiments, the zero-mode waveguide device further includes a first electrode disposed in each first chamber, a second electrode disposed in the second chamber, and a voltage source configured for providing a user-defined voltage between the first and second electrodes.

A further aspect of the invention is a system containing the zero-mode waveguide device described above, a fluorescence microscope, an image acquisition device, a processor, and a memory. The system can be used to analyze individual biomolecules by fluorescence, and further can be used to simultaneously analyze one or more biomolecules in each first fluid chamber by obtaining fluorescence imaging data.

Still another aspect of the invention is a filter or filtration system that includes the nanoporous membrane described above. The nanoporous membrane can be used in a method of water purification by retaining solutes and particulates, either entirely or selectively, through the inclusion of selected nanopores in the membrane. The density, diameter, length, charge, hydrophilicity/hydrophobicity and other chemical properties of the pores can be selected according to the filtration application.

Another aspect of the invention is a method of sequencing a nucleic acid. The method includes the steps of: (a) providing the system described above and a sample containing the nucleic acid for sequencing, or fragments thereof; (b) adding aliquots of the sample to first fluid chambers of the zero-mode waveguide device; (c) applying a negative potential to the first electrode and a positive potential to the second electrode, whereby the nucleic acid or fragments thereof migrate toward the membrane; and (d) sequencing the fragments using a fluorescence-based single molecule real time sequencing method, such as are known in the field.

The invention can further be summarized by the following list of embodiments.

1. A nanoporous membrane comprising a plurality of nanopores through the material; wherein the nanopores have a diameter in the range from about 0.3 nm to about 15 nm and provide ion conductive pathways across the membrane.

2. The nanoporous membrane of embodiment 1 comprising a material selected from the group consisting of aluminum oxide, hafnium oxide, silicon dioxide, and titanium oxide.

3. The nanoporous membrane of embodiment 1 having a specific conductance of about 10000 $S/m^2$.

4. The nanoporous membrane of embodiment 1 having a thickness in the range from about 2 nm to about 50 nm.

5. The nanoporous membrane of embodiment 1, wherein the ion conductive pathways are in the form of straight or tortuous channels through the membrane.

6. The nanoporous membrane of embodiment 1 formed by a process comprising reactive ion etching, wet chemical etching, atomic layer deposition, or molecular layer deposition.

7. A zero-mode waveguide device comprising first and second fluid chambers separated by the nanoporous membrane of embodiment 1.

8. The zero-mode waveguide device of embodiment 7, wherein the first fluid chamber has a width in the range from about 60 to about 200 nm and a depth from about 50 to about 150 nm, and is open at a top end to provide access to a fluid in the fluid chamber.

9. A zero-mode waveguide device comprising a plurality of first fluid chambers disposed in a two-dimensional array on a single chip and a single common second fluid chamber, the first and second fluid chambers separated by the nanoporous membrane of embodiment 1.

10. The zero-mode waveguide device of embodiment 9, further comprising a first electrode disposed in each first chamber, a second electrode disposed in the second chamber, and a voltage source configured for providing a user-defined voltage between said first and second electrodes.

11. A system comprising the zero-mode waveguide device of embodiment 10, a fluorescence microscope, an image acquisition device, a processor, and a memory.

12. A filter or filtration system comprising the membrane of embodiment 1.

13. A method of sequencing a nucleic acid, the method comprising the steps of:
   (a) providing the system of embodiment 11 and a sample comprising fragments of said nucleic acid;
   (b) adding aliquots of the sample to first fluid chambers of the zero-mode waveguide device;
   (c) applying a negative potential to the first electrode and a positive potential to the second electrode, whereby the fragments of said nucleic acid migrate toward the membrane; and
   (d) sequencing the fragments using a fluorescence-based single molecule real time sequencing method.

14. The method of embodiment 13, wherein the sample comprises fragments representing the genome, exome, or transcriptome of a single cell or a portion thereof.

15. The method of embodiment 14, whereby substantially the entire genome, exome, or transcriptome of the cell is sequenced.

16. A method of making the zero-mode waveguide device of embodiment 7, the method comprising the steps of:
   (a) depositing a layer of silicon nitride over an aperture in a silicon substrate;

(b) depositing a membrane layer onto the layer of silicon nitride;

(c) removing the silicon nitride layer while leaving the membrane layer intact and serving as the membrane of the device;

(d) forming a plurality of nanopores in the membrane; and (e) depositing the first chamber of the device onto the membrane.

17. The method of embodiment 16, wherein the step of (b) depositing a membrane layer comprises atomic layer deposition or molecular layer deposition carried out under conditions such that defects are included that create the plurality of ion conductive pathways through the membrane.

18. The method of embodiment 16, wherein the step of (d) forming a plurality of nanopores in the membrane is performed during or after step (c) and comprises carrying out reactive ion etching.

19. The method of embodiment 18, wherein the silicon nitride layer is removed by a dry etching technique which creates a plurality of nanopores in the membrane.

20. The method of embodiment 16, wherein the silicon substrate comprises a void below said aperture which forms the second fluid chamber of the zero-mode waveguide of the device.

21. The method of embodiment 16, which does not include forming individual pores in the membrane by an electron beam, an ion gun, or a laser.

BRIEF DESCRIPTION OF THE DRAWINGS

FIG. 1A is a schematic illustration of a silicon chip with an array of NZMWs fabricated in a layer of aluminum on a silicon nitride membrane containing nanopores (not to scale). FIG. 1B shows transmission electron micrograph (TEM) images of two typical NZMWs. FIG. 1C shows modeling of how an applied electric field extends outside the NZMW when 800 mV is applied (arrows indicate an attractive electric field for nucleic acids). FIG. 1D shows fluorescence vs. time traces with voltage capture of 230 pM 6 kbp DNA with YOYO-1 upon application of V=±850 mV. Only the NZMW captures DNA, whereas ZMWs without a nanopore do not (traces shown for 3 of about 100 ZMWs). FIG. 1E shows false-color fluorescence snapshots of a 2×4 NZMW array (in area bounded by dashed square) during stochastic capture/rupture of a fluorescently-labeled 1 kbp DNA/Alexa647-streptavidin complex.

FIG. 2A is a schematic illustration of an embodiment of a fabrication process for $SiO_2$-encapsulated NZMWs (not to scale). FIG. 2B shows a TEM image of a $SiO_2$-encapsulated ZMW after 10 minutes of boiling in piranha solution (13 nm $SiO_2$ coating clearly seen around aluminum layer, scale bar=100 nm). FIG. 2C shows photoluminescence spectra of the same device before (upper trace) and after (lower) SiN removal (excitation wavelength=488 nm).

FIG. 3A shows a scanning electron microscope (SEM) micrograph of a ZMW array with 4 NZMWs (inset shows picture of chip). FIG. 3B shows an illustration of the microscope setup for recording fluorescence from the NZMWs, and a two-probe experiment to demonstrate Stv/DNA loading and binding to the bottom of the NZMWs. FIG. 3C shows a false color overlay of fluorescence spectra in a 1×4 NZMW array (circles indicate position) surrounded by ordinary ZMWs (lacking nanopores, pale yellow circles). DNA (1.5 kbp, 17 pM) binding was observed at 250 mV within 5-10 seconds, followed by slow YOYO-1 bleaching at 0 mV for 3 NZMWs. FIG. 3D shows fluorescence images before (left) and after (right) loading and binding of Stv/λ-DNA to a 5×5 NZMW array.

FIG. 4A shows a ZMW on a nanoporous membrane as grown by molecular layer deposition (MLD). FIG. 4B shows the modeled electric field profile around a NZMW with a single 4 nm diameter pore (top) and a 3×3 array of 1 nm pores (bottom). FIG. 4C shows photoluminescence spectra of an MLD layer (lower), and of similar thickness silicon nitride (upper) for comparison. FIG. 4D shows fluorescence images of $Ca^{2+}$/Fluo-8 complexation across the membrane when voltage is applied, showing uniform porosity across the membrane.

FIGS. 5A-5D illustrate DNA loading and sequencing in NZMWs. FIG. 5A is a schematic illustration of SMRT sequencing using phospholinked fluorescent nucleotides in a NZMW. FIG. 5B shows training spectra of individual 10 pM dye solutions for four differently colored nucleotide analogs (A, C, G, and T), measured using a NZMW (dashed lines are fits). FIG. 5C shows total fluorescence vs. time in a control experiment, sequencing a 72-nt circular template+primer, where the DNA/polymerase complex is voltage-loaded onto the membrane, $Mg^{2+}$ is added to initiate sequencing, and KCl is added to halt sequencing. FIG. 5D shows a raw spectrogram excerpt (appended real-time fluorescence spectra vs. time) of 20 kbp SMRTbell captured in a NZMW, and a sample 11-mer BlastN perfect match between the subject and query 1 sequences, CGATACTGACG (SEQ ID NO: 1) obtained by applying base-calling software to the raw data.

FIGS. 6A-6B show a schematic illustration of nucleic acid loading in a multipore NZMW according to the invention. FIG. 6A shows the nucleic acid distribution in the absence of an applied voltage, and FIG. 6B shows the nucleic acid distribution in the presence of a negative potential at the NZMW side (i.e., first chamber containing the nucleic acid and positive potential at the other side of the membrane (i.e., second chamber side).

DETAILED DESCRIPTION OF THE INVENTION

Figures 1A, 1B, 1C, 1D, 1E:
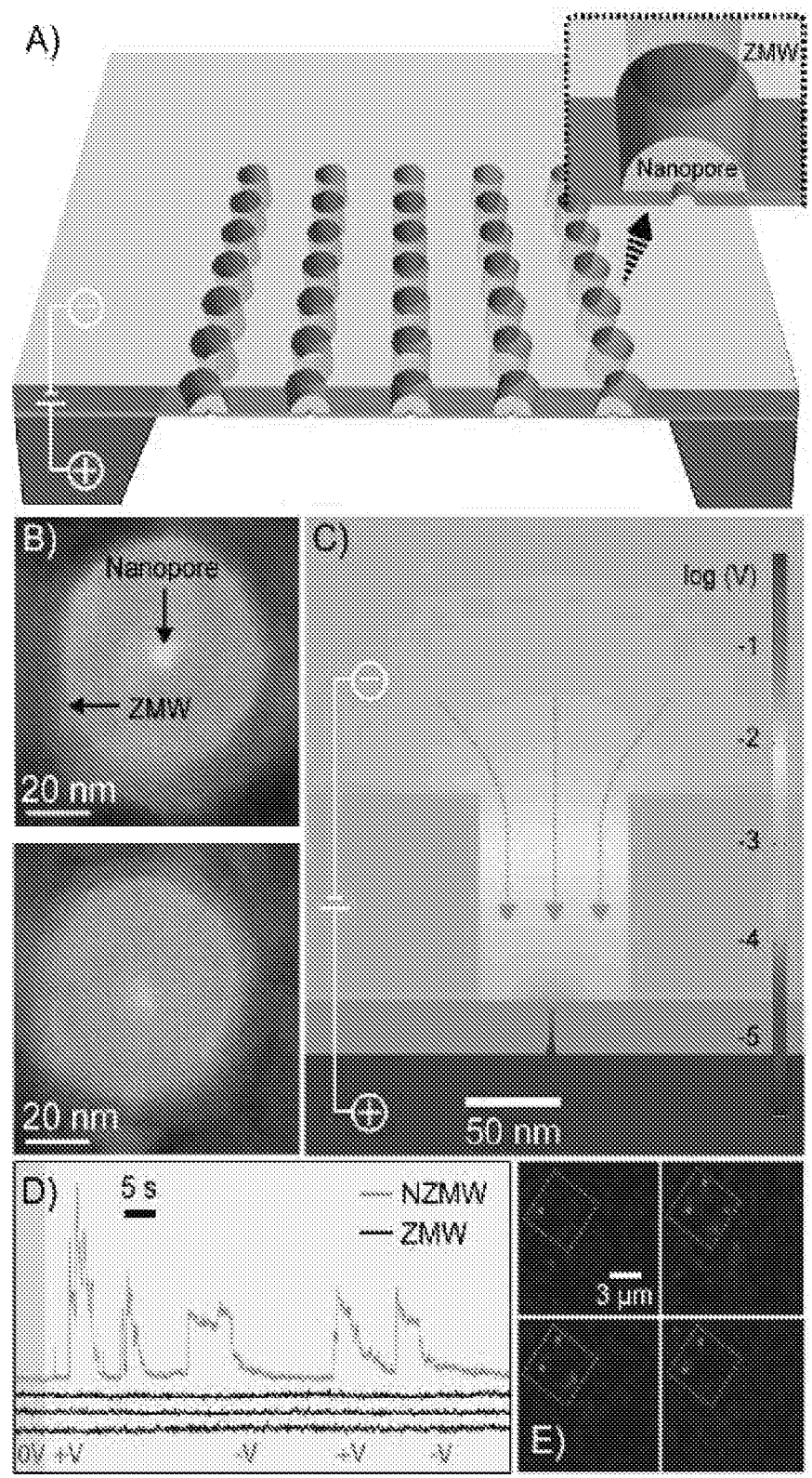
FIGS. 1A-1E show an array of NZMWs and its use in DNA and DNA/protein capture.

The inventors have developed a highly efficient method for sequencing minute quantities of nucleic acids without the need for creating a DNA library, down to quantities obtained from single cells, and devices for practicing the method. The method utilizes large arrays of nanopore zero-mode waveguides (NZMWs) for simultaneous parallel sequencing of single DNA and RNA molecules using fluorescent-labeled nucleotides and a polymerase drawn to the bottom of the NZMWs by electrophoresis. The methods are easily scalable and provide faster and cheaper sequencing than current methods.

The method and devices of the invention are made possible by the parallel fabrication of nanoporous membranes of appropriate porosity for use in nucleotide sequencing. The membrane fabrication process of the invention obviates the need for serial nanopore formation. The invention utilizes anisotropic etching techniques, such as reactive ion etching, or deposition of non-ideal thin films with controlled defects, giving rise to membranes with a plurality of nanometer scale or sub-nanometer scale pinholes. By then fabricating NZMW chambers onto these membranes it is possible to create large arrays of NZMWs with two or more pinholes at the base of each chamber. In methods of the prior art utilizing a single nanopore per NZMW well or chamber, the nanopore acts merely to provide a conduit for ion transport, allowing a suitable electric field profile to be established so that the nucleic acid and sequencing machinery are rapidly attracted to the base of the NZMW chamber. In methods of the invention, a membrane with a porosity that matches that of the single pore case, yet is derived from a plurality of pinholes, nanopores, or nanochannels, serves the same role as the single, larger nanopore of earlier methods. By applying a voltage bias across the membrane (i.e., across all pinholes in the membrane) it is possible to localize nucleic acid, nucleotide, and protein molecules at the base of the NZMWs without the need for, or the possibility of, the molecules translocating through the membrane.

The nanoporous membranes of the present invention are ultrathin and are fabricated as freestanding membranes supported at their perimeter by a support structure. The membranes are typically just a few atomic or molecular layers in thickness, and preferably have a thickness in the range from about 2 nm to about 50 nm, or from about 2, 3, 4, 5, 7, 10, 12, or 15 nm to about 5, 10, 15, 20, 25, 30, 40, or 50 nm. The membrane material is preferably an inorganic material, such as a metal oxide or other oxide. Preferred membrane materials are aluminum oxide, hafnium oxide, silicon oxide, and titanium oxide; however, any composition containing one or more metal oxides, metal nitrides, or any combination thereof can be used. Preferably the membrane material is one that can be fabricated by atomic layer deposition or molecular layer deposition, and/or is amenable to the formation of nanopores by bulk treatment of the material, such as by dry etching (e.g., reactive ion etching using a plasma) or wet chemical etching. The membrane material is preferably a non-conductive and ion-impermeable material, except for the permeation of ions through nanopores in the membrane. The membrane is fabricated within the NZMW device or added to the device in a manner such that current leakage around the membrane is essentially prevented or non-existent; substantially the only pathway for ions to traverse the membrane should be through the nanopores of the membrane.

The surface area or diameter of the membrane will generally coincide with the cross-sectional area or diameter of the NZMW upper chamber, although it may be less. Such chambers are generally circular or square in cross-section, but may have other shapes, such as elliptical, rectangular, triangular, hexagonal, or irregular. Generally, the NZMW chamber is open or partially open at the top to allow access by fluid handling equipment, and the membrane forms the floor of the chamber. The membrane is sealed to the NZMW chamber, such as by an o-ring, an adhesive, or a covalent or non-covalent bond or attractive force, so that fluid can be retained in the chamber without leakage. The width of the upper fluid chamber can be from about 60 nm to about 200 nm, or from about 60, 70, 80, 90, 100, 120, or 150 nm to about 80, 90, 100, 120, 150, 180, or 200 nm. The depth of the upper fluid chamber can be from about 50 nm to about 150 nm, or from about 50, 60, 70, 80, 90, or 100 nm to about 80, 90, 100, 120, or 150 nm. In keeping with its function as a ZMW, the upper chamber must be smaller in all dimensions than the wavelength of light used to measure fluorescence of molecules within the chamber. A NZMW device according to the invention can have 1 or more, 10 or more 100 or more, 1000 or more, 10000 or more, 100000 or more, or 1000000 or more individual NZMW upper chambers, which can be arranged in a regular geometric pattern, such as a square, rectangle, or hexagonal packing pattern, for example. Preferably, such an array shares a single common lower chamber, which is used merely to provide an electrode chamber for establishing an electrical potential across the membranes of the NZMWs, and as a reservoir for ions traversing the membrane.

The attributes of pores in the membrane (such pores are referred to herein as "nanopores", "nanochannels", or "pinholes") can be established or adjusted through the membrane fabrication process. The pore density (i.e., the number of pores per unit surface area) is adjusted such that one or more, and preferably 2 or more, 3 or more, 4 or more, 5 or more, 6 or more, 7 or more, 8 or more, 9 or more, or 10 or more, or 2-3, 2-5, 2-7, 3-5, 3-7, 3-9, 3-10, 3-12, 5-7, 5-10, or 5-15 nanopores are found within each NZMW of a NZMW device. Preferably the density of pores is essentially constant across a device, but in certain embodiments the pore density can differ across an array of NZMWs. Nanopores can have different geometries. They can be circular in cross-section, or have other shapes, including an irregular cross-section (the nanopore diameters herein refer to the maximum diameter or cross-sectional dimension). The length of the nanopores also can vary from the thickness of the membrane, to larger, particularly if the pore is not straight but has a tortuous or irregular pathway through the membrane. Nanopores can be straight (i.e., cylindrical), slanted, curved, or tortuous (i.e., following an irregular but continuous path through the membrane).

Figures 4A, 4B, 4C, 4D:
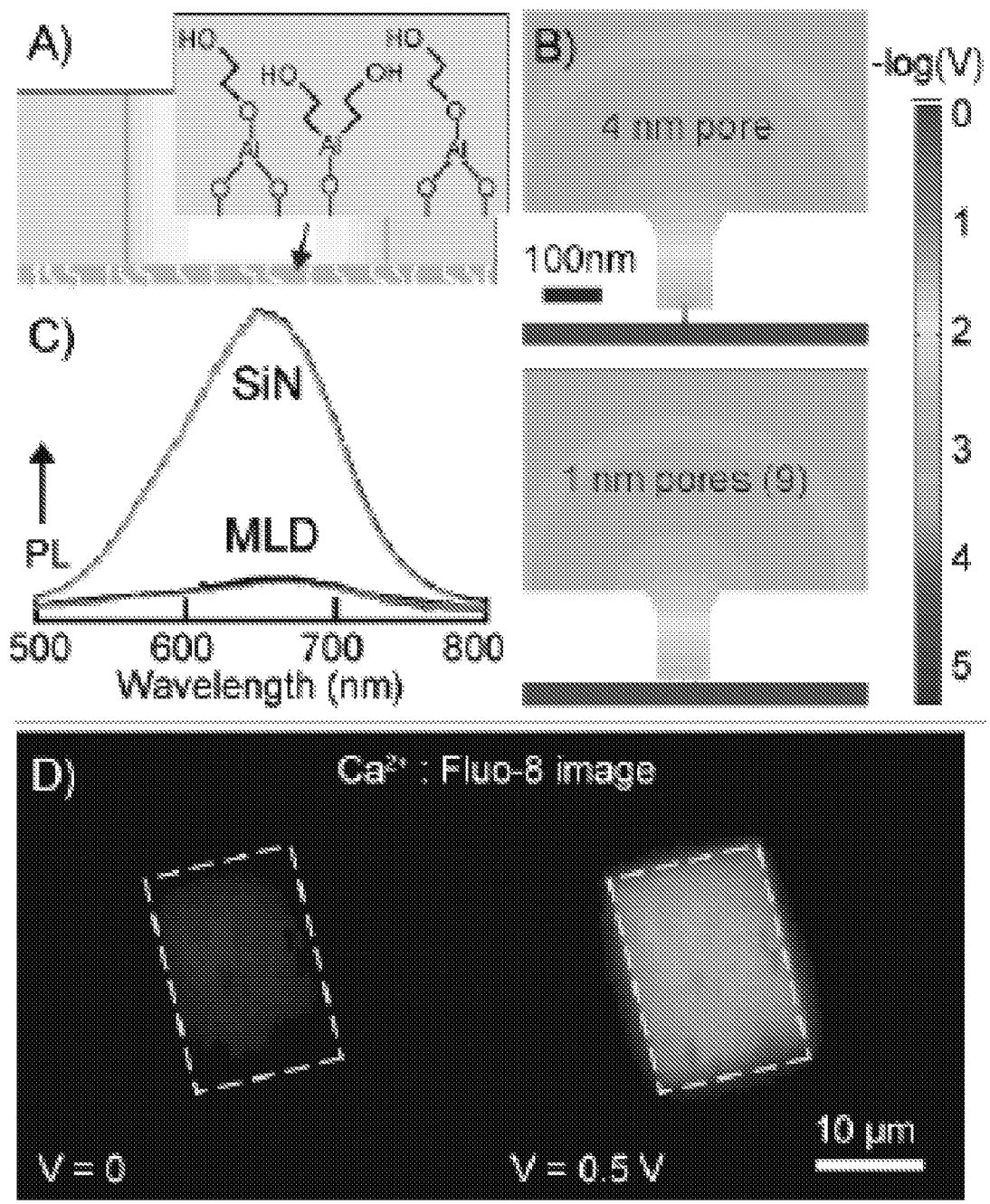
FIGS. 4A-4D show scalable alternatives to single-pore NZMWs.

While NZMWs have shown exceptional promise for picogram DNA and RNA capture, time consuming serial nanopore fabrication in registry with a large array of NZMWs, as practiced in the prior art, is a significant consideration in terms of fabrication costs, and would seriously impede mass production. Finite-element simulations indicate that having multiple smaller pores, for example, 9 pores that are 1 nm in diameter, produces a similar electric field outside the pore compared to a single 4 nm pore (see FIG. 4B). To realize such structures, the invention utilizes atomic layer deposition (ALD) or molecular layer deposition (39) techniques that produce ultrathin conformal materials with controlled composition. In MLD, a volatile organic layer is co-deposited within an inorganic matrix. When the volatile organic layer decomposes, a thin porous layer forms. In the experiment shown in FIG. 4C, a mechanically stable 8 nm thick membrane layer was formed, which had low photoluminescence and exhibited an ion conductance of $10^4$ $S/m^2$ in physiological electrolyte. A specific conductance of $10^4$ $S/m^2$ is suitable for use in nucleic acid sequencing in the NZMW, and membranes having a specific conductance at least in the range from about $10^3$ $S/m^2$ to about $10^5$ $S/m^2$ are acceptable. $Ca^{2+}$ fluorescence imaging (FIG. 4D) demonstrated that the pore distribution was uniform across the membrane.

FIGS. 6A and 6B illustrate the use of a nanoporous membrane 50 of the invention containing a plurality of nanopores 40. Nucleic acid molecules 60 rapidly migrate toward the membrane due to the electric field established by applying a voltage between first electrode 70 in the first chamber and second electrode 80 in the second chamber, negative in the first chamber and positive in the second chamber.

EXAMPLES

Example 1. Fabrication and Testing of Nanopore Zero-Mode Waveguides

Nanopore zero-mode waveguides (NZMWs) were fabricated by incorporating nanopores into ZMWs and were found to be an effective tool for capturing long DNA fragments and DNA/protein complexes (33). Prototype NZMW devices were fabricated on silicon nitride (SiN) freestanding membranes (approx. 100×100 µm squares) deposited over an aperture in a silicon chip. To make the ZMW compartments, a 100-nm-thick aluminum layer was deposited onto the SiN membrane and a hole pattern was defined using electron-beam lithography on a 4" wafer scale (total of about 280 devices). Subsequently, a single nanopore was fabricated through the SiN membrane of each ZMW using a focused electron beam of a TEM to form NZMW sub-arrays (FIGS. 1A, 1B). The nanopores were approximately 3-5 nm in diameter. Finite-element simulations (FIG. 10) showed that applied voltage across the NZMW is expected to produce trans-pore counterion flux that prescribes an electric field profile outside the ZMW area. DNA in the top chamber was efficiently captured in the NZMWs when a positive voltage is applied to the bottom chamber, while capture is not observed in ordinary ZMWs (i.e., identical chambers but not containing any nanopore). The results of DNA capture are shown in FIG. 1D. Voltage loading of DNA/protein complexes was performed in parallel using several NZMWs (FIG. 1E). ZMWs without pores at their bottom did not capture DNA at these low concentrations because hours of reaction time are needed for diffusive loading, and the process is biased towards short DNA capture in such cases.

Example 2. Improved NZMW Stability and Optical Properties

Figures 2A, 2B, 2C:
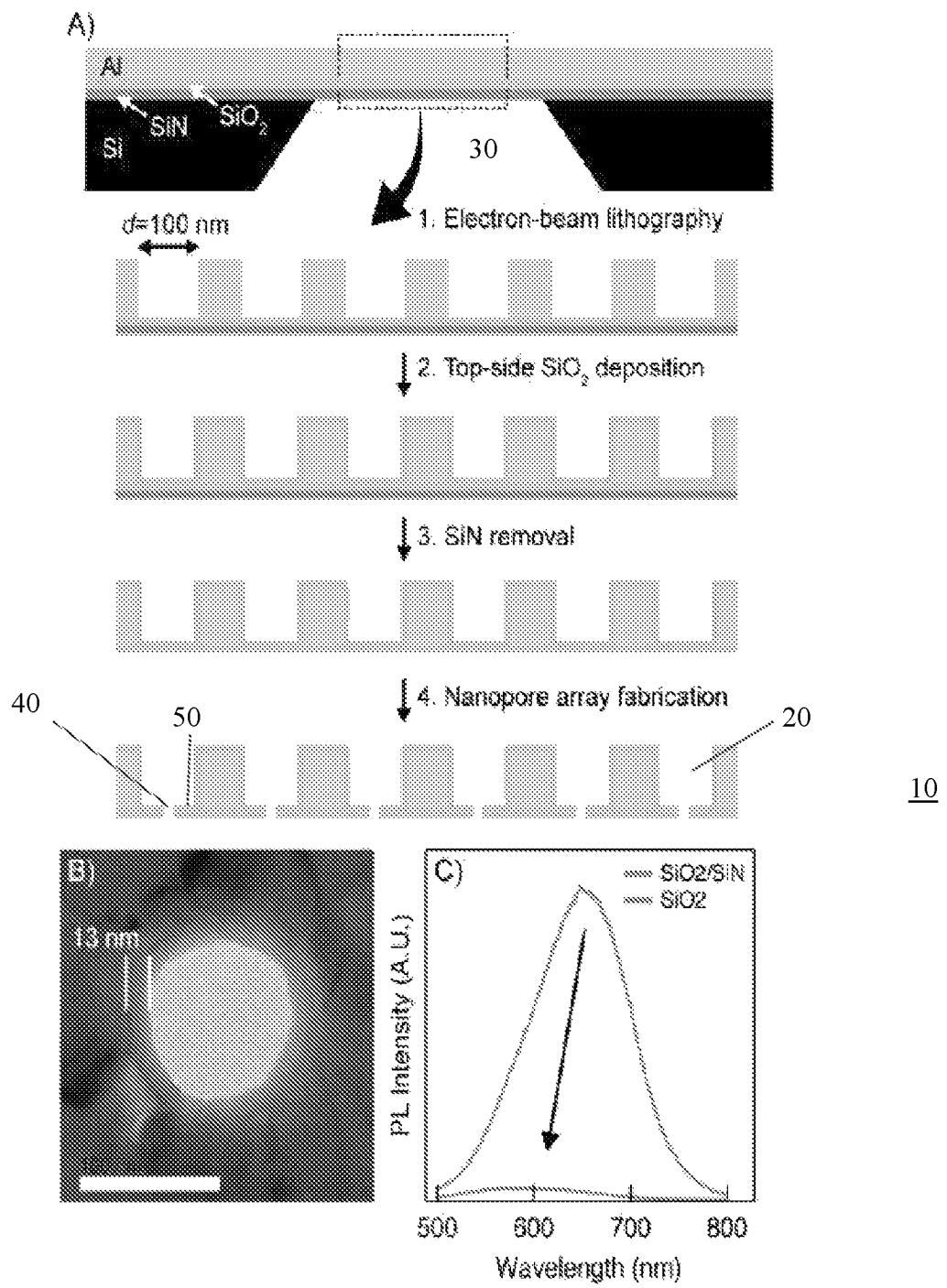
FIGS. 2A-2C show fabrication and testing of an array of NZMWs.

A main drawback of the SiN membranes described in Example 1 is their intrinsic photoluminescence, which produces a high fluorescence background in the visible spectrum and noticeably reduces the signal-to-background ratio of single fluorescent dyes (see FIG. 1E). Photoluminescence can be reduced by controlled SiN thinning and/or removal (34, 35). ZMWs were coated with 13 nm thick silica ($SiO_2$) using atomic layer deposition, followed by removal of the SiN layer using reactive ion etching and nanopore fabrication (shown schematically in FIG. 2A). The array 10 of NXMWs includes a number of adjacent first fluid chambers 20, separated by membrane 50, containing nanopore 40, from the second fluid chamber 30 below the membrane. All of these steps were performed on a 4" wafer scale, except for nanopore fabrication. The $SiO_2$ layer was found to protect the aluminum such that the chips could be cleaned with piranha solution with no degradation in the NZMW structure (see FIG. 2B), and no compromise in the mechanical stability of the membranes was observed. Most importantly, SiN removal resulted in a 20-fold reduction of background photoluminescence (FIG. 2C), to a low level that can allow 4-color fluorescent dye detection as required for sequencing.

Example 3. Quantification of DNA and RNA Capture into NZMWs

Capture of DNA into nanopores is a strong function of applied voltage, nanopore diameter, and electrolyte ionic strength (36). Efficient capture occurs due to a long-range electric field that is sculpted by ion flux profiles across the pore when voltage is applied. Larger molecules are captured at longer distances from the pore than shorter DNA molecules, such that capture rates are not biased towards shorter DNA lengths of the same mass (37). For SMRT sequencing, DNA does not need to be captured inside the nanopore, but instead needs to react with a biotin group immobilized at the ZMW base. Given high association rates of biotin to streptavidin (Stv, $k_{on}=10^7$ $M^{-1s-1}$) (38), a timescale of <1 ms is sufficient for biotin/Stv association in the confined NZMW chamber.

A two-color fluorescence spectroscopy measurement was performed on a biotin-functionalized NZMW array to investigate whether voltage-induced DNA capture into NZMWs is accompanied by reaction with biotin groups. A chip was fabricated in which 4-5 nm diameter nanopores were made in four selected ZMWs (FIG. 3A), and the surface was functionalized with PEG-biotin groups such that multiple biotin sites were available on the NZMW surface. Then, capture was tested of 17 pM biotinylated 1.5 kbp DNA intercalated with YOYO-1 and bound to Alexa647-labeled Stv. The NZMW device was mounted onto an inverted microscope equipped with a fiber-coupled three-laser excitation source, confocal pinhole array, prism dispersive element, and emCCD camera (see FIG. 3B).

Figures 3A, 3B, 3C, 3D:
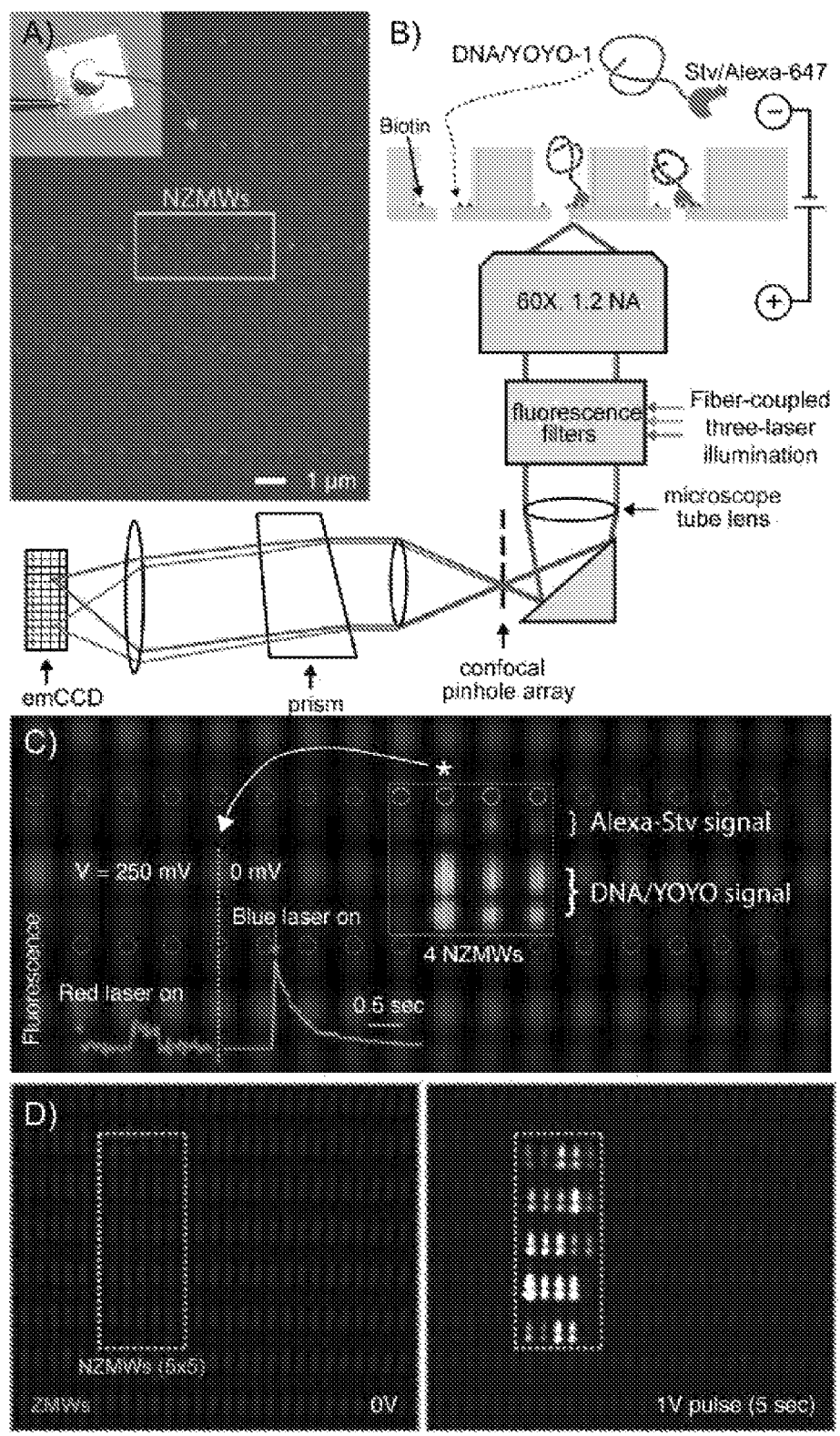
FIGS. 3A-3D show DNA capture into NZMWs.

A potential of 250 mV was first applied for 5 seconds, and Stv/Alexa-647 signals were observed in all four NZMWs that correspond to single/few dye behavior (FIG. 3C, red laser-induced trace in inset). Then, the voltage was switched off and the blue laser was turned on to probe DNA capture. A false-color overlay of the integrated fluorescence from the recorded movies is shown in FIG. 3C. Three out of four NZMWs showed YOYO-1 bulk bleaching signals (FIG. 3C, blue laser-induced trace in inset), indicating that Stv/DNA binding to surface biotins inside the NZMWs was successful. Temporal intensity variations in the DNA fluorescence are a result of interplay between DNA coil dynamics and YOYO-1 bleaching rates (see also FIG. 1D).

Capture and immobilization of 48 kbp λ-DNA into NZMWs was very efficient. In FIG. 3D the time-integrated fluorescence images of a 5×5 NZMW array are shown, before and after loading 9 pM YOYO-1 intercalated, doubly-biotinylated λ-DNA pre-bound to Stv. Within 5-10 seconds of applying 1V, 23 of the 25 NZMWs were loaded with DNA, which corresponds to a 92% yield. None of the surrounding ZMWs showed λ-DNA binding during the course of the experiment. Loading rates in units of $pg^{-1}$ $min^{-1}$ based on repeated experiments with different DNA and RNA molecules are summarized in Table 1 (±10%). Given the linear capture/concentration relationship in pores (34), it can be extrapolated that loading 1 pg input DNA would require 10 minutes on average (1 pg/µl loading solution). RNA loading was also efficient, and ribosomal RNA capture (1,500-2,900 nt) from 1 pg input levels would be expected to proceed in just under 3 minutes (1 pg/µl solution).

TABLE 1

Loading rates ($d_{NZMW}$ = 100 nm, V = 0.5-1 V).

| Analyte (Conc.) (pg/µL) | Rate ($min^{-1}$) | Loading Rate* ($pg^{-1}min^{-1}$) |
|---|---|---|
| λ-DNA, 48-kbp (160) | 18 | 0.12 |
| †Stv-bio-λ-DNA (350) | 41 | 0.11 |
| 19-kbp SMRTbell (250) | 22 | 0.09 |
| E coli rRNA, 16 + 23S (100) | 36 | 0.36 |

*1 µl sample loading volumes.
†Streptavidin-biotin-λ-DNA.

Example 4. Fabrication of Nanoporous Aluminum Oxide Membrane

A nanoporous membrane was fabricated with porosity that matches that of the single nanopore membranes and can replace single nanopore NZMWs in sequencing applications. To realize such structures, molecular layer deposition (MLD, ref. 39) was used to produce an ultrathin membrane such as that depicted in FIG. 4A. In the MLD technique, a volatile organic layer (in this case, using $AlMe_3$ precursor) is co-deposited within an inorganic matrix. When the volatile organic layer decomposes (in this case releasing ethylene oxide), a thin porous layer forms (here, a layer of $Al_2O_3$). Finite-element simulations of such membranes indicate that having multiple smaller pores, for example, 9 pores that are 1 nm in diameter, produces a similar electric field outside the pore compared to a single 4 nm pore (see FIG. 4B). The 8-nm-thick layer of $Al_2O_3$ was mechanically stable and had low photoluminescence (FIG. 4C), and exhibited an ion conductance of $10^4$ $S/m^2$ in physiological electrolyte solution. $Ca^{2+}$ fluorescence imaging across these pores demonstrated that the porous layer was spatially uniform across the membrane and is suitable as an alternative to using single nanopores. The $Al_2O_3$ layer did not etch in a $SF_6$ plasma, demonstrating that freestanding SiN can be used as a sacrificial support layer for the film, which can be etched away after membrane formation, leaving behind the porous MLD layer.

Example 5. DNA Sequencing in NZMWs

DNA sequence readout was demonstrated in a single nanopore NZMW device (see schematic illustration in FIG. 5A). Different phospholinked fluorescent nucleotides were first added to NZMW chambers, and their spectra were recorded using an emCCD camera (FIG. 5B). A circular DNA template was loaded, and sequencing was initiated following the addition of $Mg^{2+}$ ions and was quenched after KCl addition (FIG. 5C).

In another experiment, a 20 kbp SMRTbell fragment with known sequence was added (4 pM, ~2 s loading time), and sequencing was observed following the addition of $Mg^{2+}$ (FIG. 5D). The temporal spectra were fitted to the training spectra of dyes, and base calling was implemented using custom developed Python-based software. A matching 11-mer stretch was found using a BlastN algorithm (FIG. 5D). The loading rate of the 20 kbp SMRTbell was at least 10,000-fold more efficient than magnetic bead loading in standard SMRT sequencing, and long DNA-insert sequencing inside the NZMW was demonstrated.

Example 6. Generation of Porous Hafnium Oxide Membranes

Figure 7:
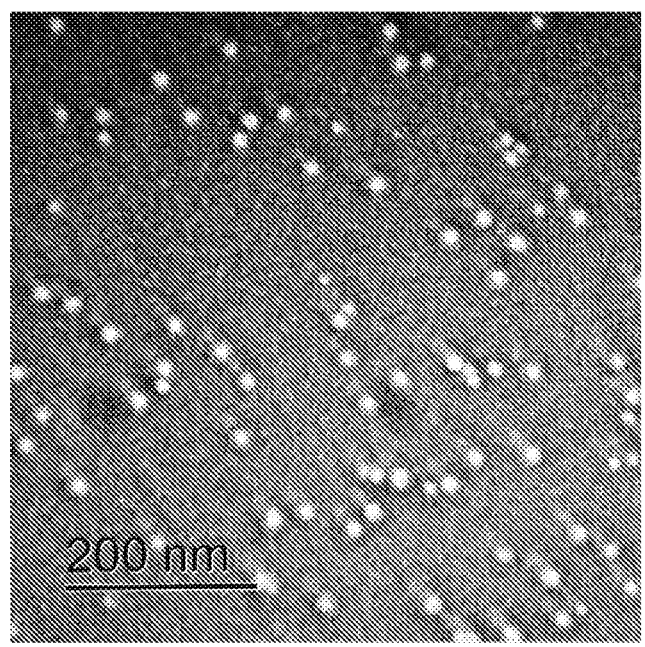
FIG. 7 shows a nanoporous hafnium oxide membrane obtained using $SF_6$ reactive ion etching of a sacrificial layer of silicon nitride adjacent to the hafnium oxide membrane.

Ultrathin nanoporous hafnium oxide membranes were fabricated. A 35 nm thick SiN membrane was suspended over a 40 µm×40 µm aperture on an aluminum support, processed using e-beam lithography to fabricate zero-mode waveguides, and then a 13 nm thick $SiO_2$ layer was deposited using atomic layer deposition. The layer was treated with piranha solution for 15 min at room temperature, followed by carrying out 40 cycles of atomic-layer deposition of $HfO_2$ at 250° C. chamber temperature. The cleaned $HfO_2$ membrane was then subjected to dry etching using $SF_6$ reactive ion etching for 1 min (the rate of etching was 30 nm/min) to remove the SiN layer and add nanopores to the $HfO_2$ membrane. The TEM image in FIG. 7 shows that the membrane contained a number of randomly distributed nanopores having a diameter of approximately 10 nm.

This application claims the priority of U.S. Provisional Application No. 62/159,731 filed 11 May 2015 and entitled "Pinhole Zero-Mode Waveguides", the whole of which is hereby incorporated by reference.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

REFERENCES

1. Bentley D R, et al., Accurate whole human genome sequencing using reversible terminator chemistry, Nature, 2008; 456(7218):53-9.
2. Wheeler D A, et al., The complete genome of an individual by massively parallel DNA sequencing, Nature, 2008; 452(7189):872-6.
3. Ley T J, et al., DNA sequencing of a cytogenetically normal acute myeloid leukaemia genome, Nature, 2008; 456(7218):66-72.
4. Wang Z, et al., RNA-Seq: a revolutionary tool for transcriptomics. Nature reviews Genetics, 2009; 10(1): 57-63.
5. Meldrum C, et al., Next-Generation Sequencing for Cancer Diagnostics: a Practical Perspective. The Clinical Biochemist Reviews, 2011; 32(4):177-95.
6. Macaulay I C, et al. G&T-seq: parallel sequencing of single-cell genomes and transcriptomes, Nat Meth, 2015; 12(6):519-22.
7. Stelzer Y, et al., Tracing Dynamic Changes of DNAMethylation at Single-Cell Resolution. Cell, 2015; 163(1): 218-29.
8. Lodato M A, et al., Somatic mutation in single human neurons tracks developmental and transcriptional history. Science, 2015; 350(6256).
9. Kellis M, et al., Defining functional DNA elements in the human genome, Proceedings of the National Academy of Sciences. 2014; 111(17):6131-8.
10. Chen R, et al., Promise of Personalized Omics to Precision Medicine, Wiley Interdisciplinary Reviews Systems Biology and Medicine 2013; 5(1):73-82.
11. LeBlanc V G, et al., Next-Generation Sequencing Approaches in Cancer: Where Have They Brought Us and Where Will They Take Us? Cancers 2015; 7(3):0869.
12. Patel A D, et al., Amplification and thrifty single molecule sequencing of recurrent somatic structural variations, Genome Research 2013; 24:318-28.
13. Norris A L, et al., Nanopore sequencing detects structural variants in cancer, Cancer Biol. Ther., 2016; 17:246-53.
14. Chaisson M J P, et al., Resolving the complexity of the human genome using single-molecule sequencing, Nature, 2015; 517(7536):608-11.
15. Pendleton M, et al., Assembly and diploid architecture of an individual human genome via single-molecule technologies, Nat Meth, 2015; 12(8):780-6.
16. Kawaji H, et al., Comparison of CAGE and RNA-seq transcriptome profiling using clonally amplified and single-molecule next-generation sequencing, Genome Research. 2014; 24(4):708-17.

17. Pretto D I, et al., Differential increases of specific FMR1 mRNA isoforms in premutation carriers, Journal of Medical Genetics, 2015; 52(1):42-52.
18. Vilfan I, et al., Analysis of RNA base modification and structural rearrangement by single-molecule real-time detection of reverse transcription, Journal of Nanobiotechnology, 2013; 11(1):8.
19. Flusberg B A, et al., Direct detection of DNA methylation during single-molecule, real-time sequencing, Nat Meth, 2010; 7(6):461-5.
20. Davis B M, et al., Entering the era of bacterial epigenomics with single molecule real time DNA sequencing, Current Opinion in Microbiology, 2013; 16(2):192-8.
21. Beaulaurier J, et al., Single molecule-level detection and long read-based phasing of epigenetic variations in bacterial methylomes, Nat Commun, 2015; 6.
22. Kazachkova N, et al., Mitochondrial DNA Damage Patterns and Aging: Revising the Evidences for Humans and Mice, Aging and Disease, 2013; 4(6):337-50.
23. Schadt E E, et al., Modeling kinetic rate variation in third generation DNA sequencing data to detect putative modifications to DNA bases, Genome Research, 2013; 23(1): 129-41.
24. Schreiber J, et al., Error rates for nanopore discrimination among cytosine, methylcytosine, and hydroxymethylcytosine along individual DNA strands, Proceedings of the National Academy of Sciences, 2013; 110(47): 18910-5.
25. Laszlo A H, et al., Detection and mapping of 5-methylcytosine and 5-hydroxymethylcytosine with nanopore MspA, Proceedings of the National Academy of Sciences. 2013; 110(47):18904-9.
26. Carlile T M, et al., Chapter Eleven—Pseudo-Seq: Genome-Wide Detection of Pseudouridine Modifications in RNA, In: Chuan H, editor, Methods in Enzymology: Academic Press; 2015. p. 219-45.
27. Pacific Biosciences Template Preparation and Sequencing Guide; Pacific Biosciences of California, Menlo Park, Calif. 2014:35.
28. Meller A, et al., Single molecule measurements of DNA transport through a nanopore, Electrophoresis. 2002; 23(16):2583-91.
29. Karlsson E, et al., Scaffolding of a bacterial genome using MinION nanopore sequencing, Scientific Reports, 2015; 5:11996.
30. Ramskold D, et al., Full-length mRNA-Seq from single-cell levels of RNA and individual circulating tumor cells, Nat Biotech, 2012; 30(8):777-82.
31. Raley C, et al., Preparation of next-generation DNA sequencing libraries from ultra-low amounts of input DNA: Application to single-molecule, real-time (SMRT) sequencing on the Pacific Biosciences RS II, bioRxiv, 25 Mar. 2014, dx.org/10.1101/003566.
32. Risse J, et al., A single chromosome assembly of *Bacteroides fragilis* strain BD from Illumina and MinION nanopore sequencing data, Gigascience, 2015; 4:60.
33. Larkin J, et al., Reversible Positioning of Single Molecules inside Zero-Mode Waveguides, Nano Letters, 2014; 14(10):6023-9.
34. Wanunu M, et al., Rapid electronic detection of probe specific microRNAs using thin nanopore sensors, Nat Nano, 2010, 5(11):807-14.
35. Assad O N, et al., Two Color DNA Barcode Detection in Photoluminescence Suppressed Silicon Nitride Nanopores, Nano Letters, 2015; 15(1):745-52.
36. Wanunu M, Nanopores: A journey towards DNA sequencing, Physics of Life Reviews, 2012; 9(2): 125-58.
37. Wanunu M, et al, Electrostatic focusing of unlabelled DNA into nanoscale pores using a salt gradient, Nat Nano, 2010; 5(2):160-5.
38. Green N M, Avidin, 1975; Adv. Protein Chem. 85-133.
39. Liang X, et al., Ultrathin highly porous alumina films prepared by alucone ABC molecular layer deposition (MLD), Microporous and Mesoporous Materials, 2013; 168:178-82.

The invention claimed is:

1. A nanoporous membrane comprising a plurality of nanopores through the material; wherein the nanopores have a diameter in a range from about 0.3 nm to about 15 nm and provide ion conductive pathways across the membrane, the membrane having a specific conductance of about 10000 S/m$^2$.

2. The nanoporous membrane of claim 1 comprising a material selected from the group consisting of aluminum oxide, hafnium oxide, silicon dioxide, and titanium oxide.

3. The nanoporous membrane of claim 1 having a thickness in the range from about 2 nm to about 50 nm.

4. The nanoporous membrane of claim 1, wherein the ion conductive pathways are in the form of straight or tortuous channels through the membrane.

5. The nanoporous membrane of claim 1 formed by a process comprising reactive ion etching, wet chemical etching, atomic layer deposition, or molecular layer deposition.

6. A device comprising a zero-mode waveguide, the device comprising first and second fluid chambers separated by a nanoporous membrane of claim 1, wherein the first and second fluid chambers and the membrane form said zero-mode waveguide, and wherein the membrane comprises a plurality of nanopores within said zero-mode waveguide that provide ion conductance pathways across the membrane.

7. The zero-mode waveguide device of claim 6, wherein the first fluid chamber has a width in the range from about 60 to about 200 nm and a depth from about 50 to about 150 nm, and is open at a top end to provide access to a fluid in the fluid chamber.

8. A zero-mode waveguide device comprising a plurality of first fluid chambers disposed in a two-dimensional array on a single chip and a single common second fluid chamber, the first and second fluid chambers separated by a nanoporous membrane of claim 1 and form a plurality of zero-mode waveguides disposed in the two-dimensional array, wherein the membrane of each waveguide of said plurality of waveguides comprises a plurality of nanopores that provide ion conductance pathways across the membrane.

9. The zero-mode waveguide device of claim 8, further comprising a first electrode disposed in each first chamber, a second electrode disposed in the second chamber, and a voltage source configured for providing a user-defined voltage between said first and second electrodes.

10. A system comprising the zero-mode waveguide device of claim 9, a fluorescence microscope, an image acquisition device, a processor, and a memory.

11. A filter or filtration system comprising the membrane of claim 1.

* * * * *

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Synthetic Construct

<400> SEQUENCE: 1
cgatactgac g                                                        11
```